United States Patent [19]

Meanwell

[11] Patent Number: 5,011,851
[45] Date of Patent: Apr. 30, 1991

[54] IMIDAZOLE CARBOXYLIC ACIDS AND ESTERS AND INHIBITION OF BLOOD PLATELET AGGREGATION THEREWITH

[75] Inventor: Nicholas A. Meanwell, East Hampton, Conn.

[73] Assignee: Bristol-Myers Squibb Co., New York, N.Y.

[21] Appl. No.: 540,988

[22] Filed: Jun. 20, 1990

Related U.S. Application Data

[63] Continuation-in-part of Ser. No. 479,506, Feb. 13, 1990, abandoned.

[51] Int. Cl.$^5$ .................. C07D 233/64; C07D 233/84; A61K 31/415
[52] U.S. Cl. .................................. 514/400; 514/398; 548/337; 548/342
[58] Field of Search ................. 514/400, 398; 548/342, 548/337

[56] References Cited

U.S. PATENT DOCUMENTS

| | | | |
|---|---|---|---|
| 4,272,543 | 6/1981 | Niedballa et al. | 548/337 |
| 4,355,040 | 10/1982 | Furukawa et al. | 548/336 |
| 4,402,960 | 9/1983 | Niedballa et al. | 548/337 |
| 4,460,598 | 7/1984 | Lautenschlager et al. | 548/336 |
| 4,668,794 | 5/1987 | Wareing | 548/342 |
| 4,686,231 | 8/1987 | Bender et al. | 514/333 |
| 4,900,744 | 2/1990 | Billheimer et al. | 548/337 |

*Primary Examiner*—Mary C. Lee
*Assistant Examiner*—Lenora A. Miltenberger
*Attorney, Agent, or Firm*—Robert H. Uloth

[57] ABSTRACT

Heterocyclic acids and esters useful as inhibitors of mammalian blood platelet aggregation characterized by Formula I or II are disclosed.

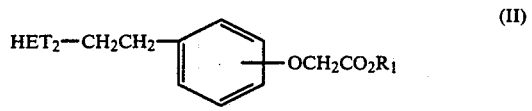

(I)

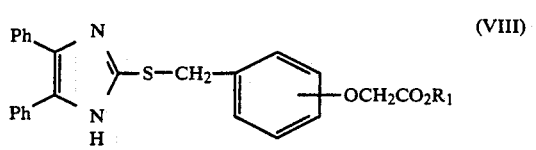

(II)

(VIII)

Formula I compounds are those wherein n is 6–9, R is hydrogen, lower alkyl or an alkali metal ion, and HET$_1$ is the heterocyclic radical 4,5-diphenyl-1H-imidazol-2-yl.

Formula II compounds are those wherein R$_1$ is hydrogen, lower alkyl or an alkali metal ion, and the radical —OCH$_2$CO$_2$R is attached in the 3 or 4 ring position; and HET$_2$ is the heterocyclic radical 4,5-diphenyl-1H-imidazol-2-yl.

Formula VIII compounds are those wherein R$_1$ is hydrogen, lower alkyl or an alkali metal ion, and the radical —OCH$_2$CO$_2$R is attached in the 3 or 4 ring position.

11 Claims, No Drawings

IMIDAZOLE CARBOXYLIC ACIDS AND ESTERS AND INHIBITION OF BLOOD PLATELET AGGREGATION THEREWITH

CROSS REFERENCE TO RELATED APPLICATION

This is a continuation-in-part of application Ser. No. 479,506, filed Feb. 13, 1990, now abandoned.

BACKGROUND OF THE INVENTION

This invention generally pertains to heterocyclic carbon compounds having drug and bio-affecting properties and to their preparation and use. In particular, the invention is concerned with various heterocyclic derivatives characterized by Formulas I and II, infra., which are inhibitors of blood platelet aggregation.

United States patents relating to the carboxylic acid and ester derivatives of the various heterocycles disclosed herein are as follows:

Imidazole compounds in Field of Search 514/396 and 548/342.

Furukawa, et al., U.S. Pat. No. 4,355,040 discloses imidazole-5-acetic acid derivatives having hypotensive properties of formula (1).

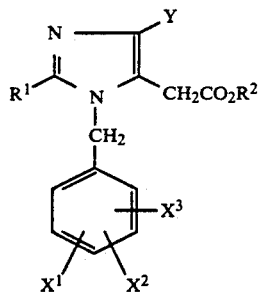
(1)

Lautenschlager, et al., U.S. Pat. No. 4,460,598 discloses triphenylimidazolyloxyalkanoic acids having antithromogenic properties of formula (2).

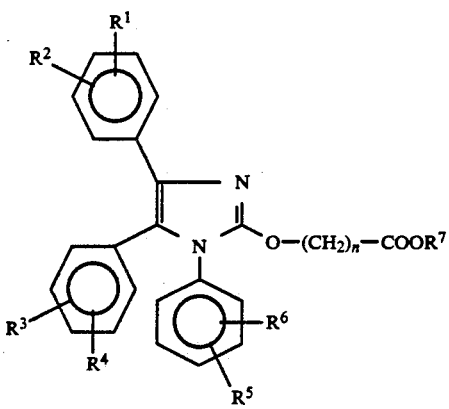
(2)

Wareing, U.S. Pat. No. 4,668,794 discloses imidazole acrolein analogs having blood cholesterol lowering properties of formula (3).

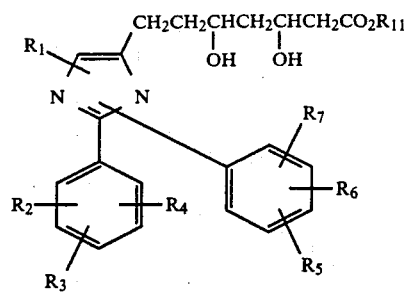
(3)

Bender, et al., U.S. Pat. No. 4,686,231 discloses 4,5-diaryl-2(substituted)-imidazoles having 5-lipoxygenase inhibiting properties of formula (4).

(4)

SUMMARY OF THE INVENTION

In its broadest aspect, this invention is concerned with heterocyclic carboxylic acids and esters of Formula I and Formula II

$HET_1—(CH_2)_nCO_2R$ (I)

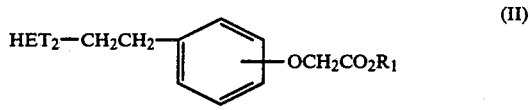
(II)

wherein $HET_1$, $HET_2$, R, $R_1$, and n are defined below which are inhibitors of adenosine diphosphate and collagen-induced aggregation of human platelet-rich plasma and are particularly useful as inhibitors of mammalian blood platelet aggregation.

Another embodiment of the invention relates to the alkali metal salts of carboxylic acids of Formula I (R is hydrogen) and Formula II ($R_1$ is hydrogen). A further embodiment concerns pharmaceutical compositions comprised of a Formula I or II compound combined with at least one pharmaceutically acceptable excipient. Yet another embodiment relates to a method for inhibiting blood platelet aggregation in a mammal which comprises administering a therapeutically effective amount of a compound of Formula I or an alkali metal salt thereof where R is hydrogen or a Formula II compound or an alkali metal salt thereof where $R_1$ is hydrogen to a mammal in need of such treatment.

DETAILED DESCRIPTION OF THE INVENTION

This invention relates to inhibitors of mammalian blood platelet aggregation of Formula I $HET_1—(CH_2)_nCO_2R$ (I)

wherein n is 6-9, R is hydrogen, lower alkyl or an alkali metal ion, and $HET_1$ is the heterocyclic radical

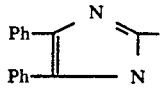

4,5-diphenyl-1H-imidazol-3-yl.

The compounds of the instant invention are further characterized by Formula II

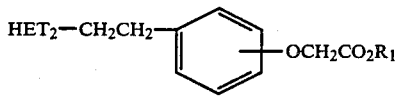

wherein $R_1$ is hydrogen, lower alkyl or an alkali metal ion, and the radical —$OCH_2CO_2R$ is attached in the 3 or 4 ring position:

$HET_2$ is the heterocyclic radical

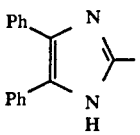

4,5-diphenyl-1H-imidazol-2-yl.

It is understood that as used herein limitations of Formula I and II are defined as follows.

The term "lower alkyl" refers to a branched or unbranched saturated hydrocarbon chain containing from 1-4 carbon atoms; specifically, methyl, ethyl, n-propyl, isopropyl, n-butyl, secondary butyl, and tertiary butyl.

The term "lower alkanol" denotes an alcohol having 1-4 carbon atoms defined by "lower alkyl".

The symbol "Ph" represents phenyl.

The term "alkali metal ion" refers to ions derived from the alkali metals, most preferably sodium and potassium.

According to the present invention the compounds characterized by Formula I are obtained by a process comprising:

(a) hydrolyzing a compound of Formula ($I^a$)

where $HET_1$ is as defined above, n is 6–9 and $R^a$ is lower alkyl, or (b) esterifying a compound of Formula ($I^b$)

wherein $HET_1$ is as defined above and n is 6–9 with a lower alkanol, or (c) alkylating $HET_1$-H wherein $HET^1$ is as defined above with a compound of Formula (III)

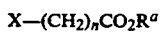

wherein X is halogen, preferably bromine, n is 6 to 9, and $R^a$ is lower alkyl.

Scheme 1 below illustrates the foregoing process.

Scheme 1

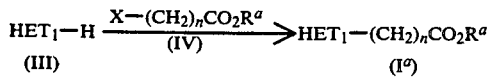

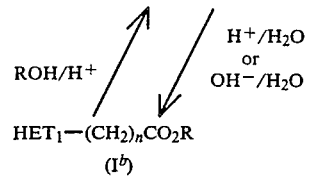

Compounds of Formula I are conventionally prepared as shown in Scheme 1 by base-mediated alkylation of the parent heterocycle (III) with a lower alkanol ester of an omega-halogenalkanoic acid (IV) to provide esters ($I^a$). Alkylation can be carried out with sodium hydride, potassium hydride, potassium t-butoxide in suitable solvents such as tetrahydrofuran and dimethylformamide with conditions dependent upon the identity of the heterocycle and the acidity of the proton being replaced. Preferred alkylating conditions employ sodium hydride in dimethylformamide (DMF) at room temperature or potassium carbonate in DMF at 110° C. In those instances where the alkylation results in mixtures of regioisomers, separation is readily accomplished by chromatography on silica gel. Structural assignments are made from consideration of the $^1H$ and $^{13}C$ NMR spectra. The heterocycles (III) employed as starting material are synthesized by methods reported in the chemical literature or by minor modifications thereof readily apparent to a skilled chemist.

Esters ($I^a$) are converted to the corresponding acids ($I^b$) under the influence of either aqueous alkali or aqueous acid depending upon the sensitivity of the heterocycle. Conversely, acids ($I^b$) are conventionally converted to the corresponding esters ($I^a$) by heating the acid in a lower alkanol in the presence of an inorganic acid such as hydrochloric, sulfuric and the like.

Alkali metal salts of Formula I carboxylic acids (R is an alkali metal ion) are conventionally prepared by dissolving the acid in a suitable solvent such as methanol, adding a molar equivalent of an alkali base such as sodium methoxide, and precipitating the salt or removing the solvent.

According to the present invention, the compounds characterized by Formula II are obtained by a process comprising:

(a) hydrolyzing a compound of Formula $II^a$

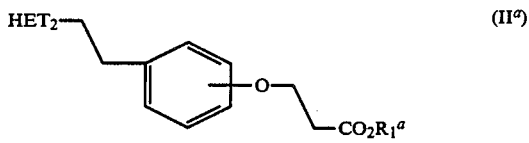

wherein $HET_2$ is as defined above and $R_1^a$ is lower alkyl; or (b) esterifying a compound of Formula $II^b$

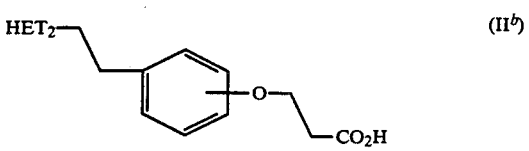

wherein $HET_2$ is as defined above; or (c) alkylating $HET_2$-H wherein $HET_2$ is as defined above with a compound of Formula V

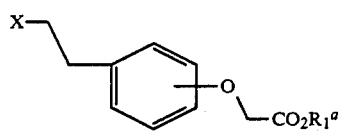

wherein $R_1^a$ is lower alkyl and X is halogen or an aryl sulfonate; or (d) alkylating a compound of Formula VI

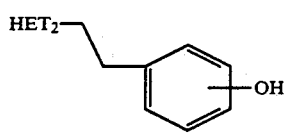

wherein $HET_2$ is as defined above with $BrCH_2CO_2R_1^a$ wherein $R_1^a$ is lower alkyl, or (e) hydrolyzing a compound of Formula VII

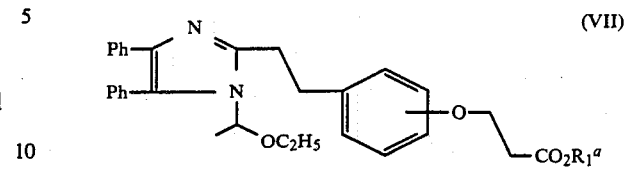

wherein $R_1^a$ is as defined above.

The following schemes for preparation of representative compounds of Formula II illustrate the foregoing process.

Scheme 2

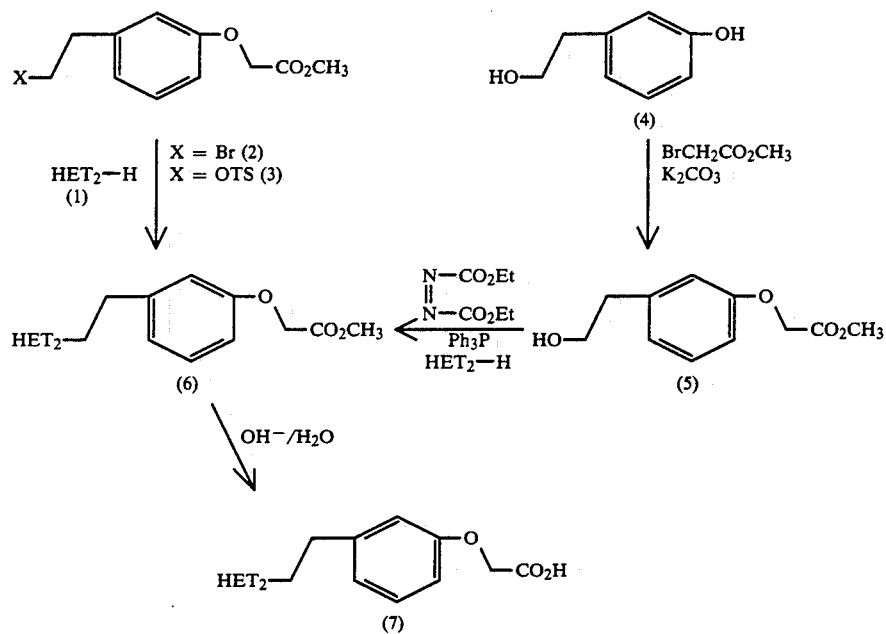

Scheme 3

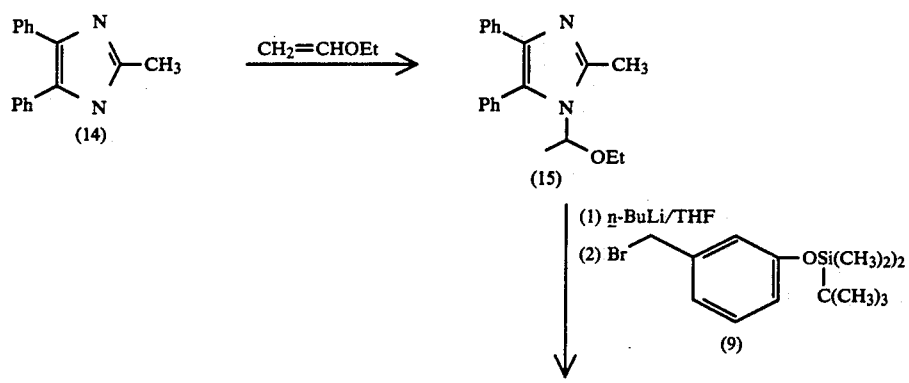

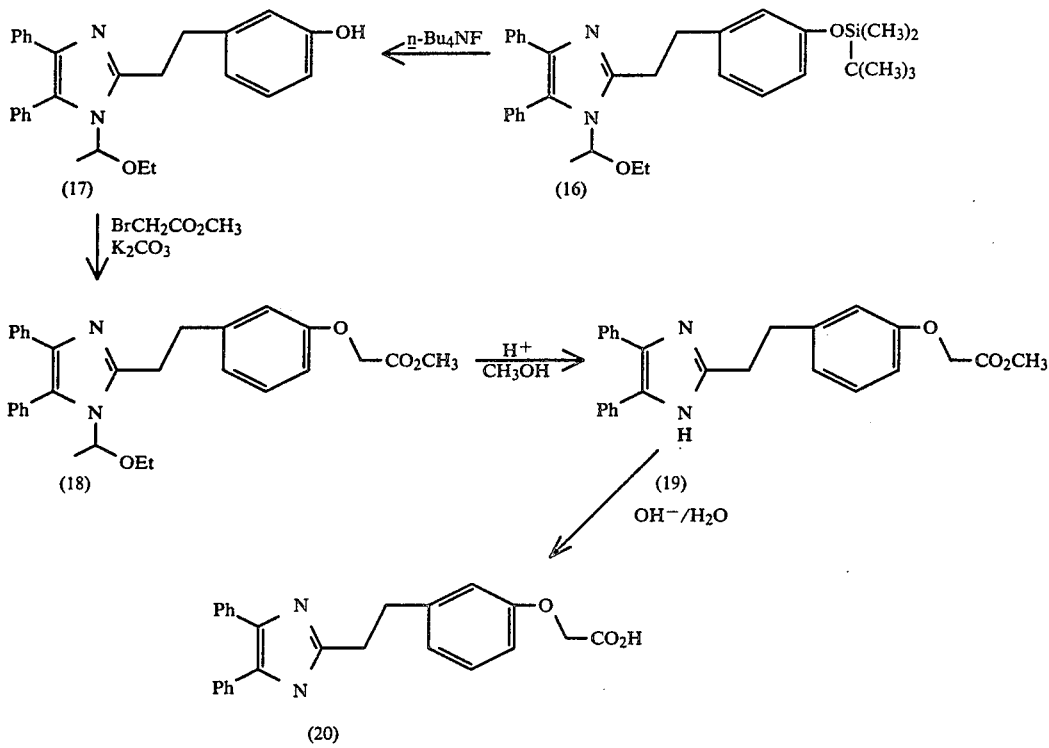

Scheme 2 depicts several different approaches for synthesis of compounds incorporating the aryloxyacetic acid moiety. Direct alkylation of heterocycle (1) with either bromide (2) or tosylate (TS) (3) available from alcohol (5), was accomplished with sodium hydride in DMF at room temperature or potassium carbonate in DMF at 110° C. to furnish esters (6). Alternatively, in some cases, reaction of the heterocycle (1) with alcohol (5) obtained from diol (4) in the presence of diethyl azodicarboxylate and triphenylphosphine provided esters (6) under the mild conditions characteristic of the Mitsunobu reaction, Synthesis, 1–28 (1981). Carboxylic acids (7) were obtained by alkaline hydrolysis of esters (6).

Scheme 3 depicts preparation of Formula II imidazole derivatives (19) and (20) wherein the aryloxyacetic acid side chain is also appended to a carbon. The presence of an active hydrogen in 2-methyl-4,5-diphenylimidazole (14) necessitated introduction of a protecting group onto one of nitrogen atoms prior to metallation. Various protecting groups known to those skilled in the art can be used with the ethoxyethyl moiety described by T. S. Manoharan, et al., J. Org. Chem., 53, 1107–1110 (1988), particularly preferred as it has the advantage of being inexpensive and easily introduced. Heating 2-methyl-4,5-diphenylimidazole (14) with an excess of ethyl vinyl ether in a sealed reaction vessel provided the crystalline N-(1-ethoxyethyl) imidazole (15). Metallation of imidazole (15) with n-butyllithium followed by reaction with bromide (9) provided silyl ether (16). Selective removal of the silyl protecting group was accomplished by exposing (16) to tetra-n-butylammonium fluoride. Alkylation of phenol (17) with methyl bromoacetate afforded ester (18) which was converted to the imidazole (19) by heating in methanol in the presence of concentrated sulfuric acid. Aqueous alkaline hydrolysis gave acid (20).

Alkali metal salts of Formula II carboxylic acids ($R_1$ is an alkali metal ion) are conventionally prepared by dissolving the acid in a suitable solvent such as methanol, adding a molar equivalent of an alkali base such as sodium methoxide, and precipitating the salt or removing the solvent.

As stated above, the compounds of Formula I and Formula II have pharmacological properties which make the particularly useful as inhibitors of blood platelet aggregation.

Platelet aggregation is considered part of a complex physiological mechanism for formation of a thrombus in the vascular system. Thromboembolic phenomena, i.e., the formation of thrombi, are involved in hemostasis and a number of disease states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few and in ischaemic heart disease, artherosclerosis, multiple sclerosis, intracranial tumors, thromboembolism, and hyperlipemia; refer to A. Poplawski, et al , J. Artherosclerosis Research, 8, 721 (1968). Thus, the compounds of the invention which have antithrombogenic actions (inhibit blood platelet aggregation) are useful in prevention or treatment of conditions involving platelet aggregation and thrombosis such as the above. The instant compounds are also considered to have antimetastatic potential in view of their platelet inhibition properties.

The pharmacological properties of the instant compounds can be demonstrated by conventional in vitro and in vivo biological tests such as the following.

IN VITRO INHIBITION OF HUMAN PLATELET AGGREGATION

The aggregometer method of Born, C.V.R., *J. Physiol.*, (London), 1962, 162, 67–68, as modified by Mustard, J. F., et al., *J. Lab. Clin. Med.* 1964, 64, 548–599 was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140 xg) from citrated (3.8%) human blood. All glassware used for preparation of PRP is silicon treated. ADP in final concentration of 0.5 meg/mL or 0.05 mL of a collagen suspension prepared according to the method described by Evans, G., et al., *J. Exp. Med.*, 1968, 128, 877–894 was used to induce aggregation. The various compounds tested were dissolved in dimethylsulfoxide (DMSO) so that 5 mol added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 meg/ml vs. ADP and 245 meg/ml vs collagen. Results for 50% inhibition of ADP-induced aggregation are given hereinafter.

TABLE 1

Inhibition of Human Platelet Aggregation
of Formula II Compounds ($IC_{50}$ mcg/ml)

$HET_2-CH_2CH_2-\text{[phenyl]}-OCH_2CO_2R_1$

| Example | $HET_2$ | $R_1$ | Vs ADP mcg/ml |
|---|---|---|---|
| 1 | 4,5-diphenyl-1H-imidazol-2-yl | $CH_3$ | 2.4 |
| 2 | 4,5-diphenyl-1H-imidazol-2-yl | H | 1.2 |

The acids are particularly potent inhibitors of ADP-induced aggregation of human platelets. While the esters are generally less active than the parent acid, they are useful as pro-drugs in vivo where they ar hydrolyzed to the corresponding acid.

The dosage employed in the therapeutic methods of the instant invention will vary with the form of administration, the particular compound chosen, the subject being tested and the effect desired. Suitable effective doses in animals range from 0.1–50 mg/kg body weight orally and from 0.05–10 mg/kg body weight parenterally (generally characterized as subcutaneous, intramuscular, and intravenous injection). It is contemplated that the effective unit dose in man will range from 1 to 100 mg and preferably from 1 to 20 mg administered one to three times a day. In accordance with conventional clinical practice, the effective dose can be determined by administering a Formula I or II compound at a dosage substantially less than the dose of the compound which is thought to be effective and then increasing the dosage in small increments until the desired effect is achieved.

In carrying out the instant therapeutic methods, the active ingredient of Formula I or II or alkali metal salts of Formula I and II carboxylic acids are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspension, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing o wetting agents and suspending agents identical or similar to those mentioned above.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Thomas-Hoover capillary melting point apparatus and are uncorrected. Proton magnetic resonance ($^1$H-NMR) spectra were recorded on a Bruker AM 300, Bruker WM 360 or Varian Gemini 300 spectrometer. All spectra were determined in $CDCl_3$ or DMSO-$d_6$ unless otherwise indicated and chemical shifts are reported in delta units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; and dd, doublet of doublet.

EXAMPLE 1

Methyl [3-[2-(4,5-diphenyl-1H-imidazol-2-yl)ethyl]phenoxy]-acetate

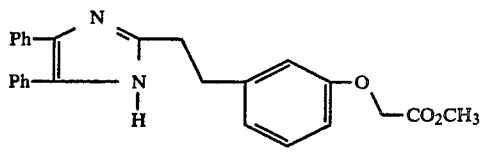

A mixture of 3-[2-[1-(1-ethoxyethyl)-4,5-diphenyl-1H-imidazo-2-yl]ethyl]phenol (6.60 g, 16 mmol), methyl bromoacetate (2.69 g, 1.66 mL, 18 mmol), potassium carbonate (2.65 g, 19 mmol), potassium iodide (catalytic amount) and acetonitrile (100 mL) was stirred at reflux for 2.5 hours. The mixture was filtered concentrated and the residual oil dissolved in methanol (120 mL). Concentrated sulfuric acid (6 drops) was added and the mixture heated to reflux. After 75 minutes, concentrated $H_2SO_4$ (3 drops) was added and the mixture heated at reflux for a further 3.75 hours. The methanol was evaporated, the residue diluted with water and saturated sodium carbonate solution and the mixture extracted with $CH_2Cl_2$. The combined extracts were dried over sodium sulfate and the solvent removed to leave an oil that crystallized on standing for 40 hours. Trituration with diethyl ether gave methyl [3-[2-(4,5-diphenyl-1H-imidazol-2-yl)ethyl]phenoxy.-acetate (5.15 g, 78%). An analytical sample was prepared by recrystallizing a sample twice from a mixture of $CH_2Cl_2$, diethyl ether and hexanes and had mp 123°–125° C.

Anal. Calcd. for $C_{26}H_{24}N_2O_3 \cdot 0.8H_2O$: C, 73.16; H, 6.05; N, 6.57; $H_2O$ 3.38. Found: C, 73.00: H, 5.78; N, 6.56; $H_2O$, 3.92%.

$^1$H-NMR (CDCl$_3$) delta: 2.80 (4H, bs), 3.71 (3H, s), 4.52 (2H, s), 6.50 to 6.70 (3H, m), 6.94 (1H, t, J=7.5 Hz), 7.15 to 7.35 (8H, m), 7.40 to 7.45 (2H, m) and 10.13 (1H, bs).

EXAMPLE 2

[3-[2-(4,5-Diphenyl-H-imidazol-2-yl)ethyl]phenoxyacetic Acid

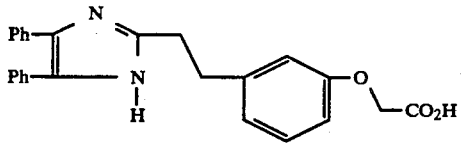

A mixture of methyl [3-(2-(4,5-diphenyl-1H-imidazol-2-yl)ethyl]phenoxy]acetate (1.20 g, 3 mmol), 5N NaOH solution (1.74 mL, 9 mmol) and methanol (30 mL) was heated to reflux on a steam bath for 20 minutes. The solvent was removed, the residue diluted with water and acidified to pH=1 with 2N HCl solution. A yellow solid was filtered off and subjected to chromatography on a column of silica gel using a mixture of chloroform and methanol (9:1) as eluent to give [3-[2-(4,5-diphenyl-1H-imidazol-2-yl)ethyl]phenoxy]-acetic acid (0.42 g, 36%), mp 244°–246° C.

Anal. Calcd. for $C_{25}H_{22}N_2O_3 \cdot H_2O$: C, 72.10; H, 5.81; N, 6.36; $H_2O$ 4.33. Found: C, 72.01; H, 5.72; N, 6.36; $H_2O$, 1.07%.

$^1$H-NMR (DMSO-d$^6$) delta: 3.03 (4H, bs), 4.63 (2H, s), 6.73 (1H, d, J=8 Hz), 6.80 to 6.90 (2H, m), 7.20 (1H, t, J=8 Hz) and 7.25 to 7.60 (10H, m).

EXAMPLE 3

Preparation of Intermediates (3-1)

1-(1-Ethoxyethyl)-2-methyl-4,5-diphenyl-1H-imidazole

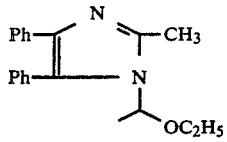

A mixture of 2-methyl-4,5-diphenylimidazole (3.00 g, 13 mmol), ethyl vinyl ether (9.23 g, 12.30 mL, 130 mmol) and hydroquinone (0.14 g, 1.2 mmol) was heated at 180° C. in a sealed vessel for 17 hours. The excess ethyl vinyl ether was evaporated and the residue chromatographed on a column of silica gel using a mixture of diethyl ether and hexanes (3:2) as eluent. Elution gave 1-(1-ethoxyethyl)-2-methyl-4,5-diphenyl-1H-imidazole (2.68 g, 68%), mp 87°–89° C.

Anal. Calcd. for $C_{20}H_{22}N_2O$: C, 78.40: H, 7.24; N, 9.14 Found: C, 78.64; H, 7.31; N, 9.56%.

$^1$H-NMR (CDCl$_3$) delta: 1.09 (3H, t, J=7 Hz), 1.55 (3H, d, J=6 Hz), 2.62 (3H, s), 3.20 and 3.35 (2H, m), 5.07 (1H, q, J=6 Hz) and 7.00 to 7.50 (10H, m).

(3-2)

3-[2-[1-(1-Ethoxyethyl)-4,5-diphenyl-1H-imidazol-2-yl]ethyl]-phenol

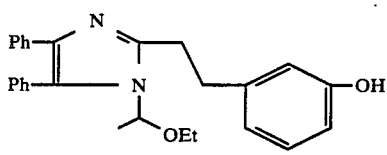

n-Butyllithium (3.89 g, 61mmol) in hexane (24.31 mL) was added dropwise to a stirred solution of 1-(1-ethoxyethyl)-2-methyl-4,5-diphenyl-1H-imidazole (15.50 g, 51 mmol) in dry THF (300 mL) maintained at −78° C. under an atmosphere of nitrogen. The mixture was stirred for 45 minutes and [3-(bromomethyl)-phenoxy]-dimethyl(1,1-dimethylethyl)silane (16.77 g, 50 mmol) added dropwise. After 10 minutes, the mixture was poured onto water, extracted with $CH_2Cl_2$, the extracts combined and dried over sodium sulfate. Evaporation of the solvent left an oil which was dissolved in THF (75 mL) and a solution of tetra-n-butylammonium fluoride (17.22 g, 66mol) in THF (65 mL) added. The solution was stirred at room temperature for 30 minutes, the solvent evaporated and the residue diluted with water. After addition of 2N HCl solution (about 20 mL) to pH=5, the mixture was extracted with $CH_2Cl_2$ The combined extracts were dried over sodium sulfate, concentrated in vacuo and the residual material chromatographed on a column of silica gel. Elution with a mixture of diethyl ether and hexanes (1.0 gave 3-[2-[1-(1-ethoxyethyl)-4,5-diphenyl-1H-imidazol-2-yl]ethyl]-phenol (8.18 g, 39%), mp 165.5°–167° C. after recrystallization from a mixture of $CH_2Cl_2$ and hexanes.

Anal. Calcd. for $C_{27}H_{28}N_2O_2 \cdot 0.4\ H_2O$ C, 77.27; H, 6.92; N, 6.68; H2O, 1.72. Found: C, 77.31: H, 6.93; N, 6.29; H2O, 1.75%.

$^1$H-NMR (CDCl$_3$) delta: 0.99 (3H, t, J=7 Hz), 1.45 (3H, d, J=6 Hz), 3.00 to 3.40 (6H, m), 5.05 (1H, q, J=6 Hz), 6.60 (1H, dd, J=7 Hz, J'=1.5 Hz), 6.74 (2H, m), 7.00 to 7.30 (4H, m), 7.30 to 7.45 (4H, m), 7.45 to 7.60 (3H, m) and 9.30 (1H, s).

SUPPLEMENTAL DISCLOSURE

The compounds of the instant invention wherein HET$_2$ is the heterocyclic radical 4,5-diphenyl-1H-imidazol-2-yl are further characterized by Formula VIII

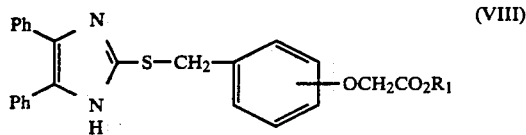

wherein R$_1$ is hydrogen, lower alkyl or an alkali metal ion and the radical —OCH$_2$CO$_2$R is attached in the 3 or 4 ring position.

Formula VIII compounds are obtained by a process comprising:

(a) hydrolyzing a compound of Formula IX

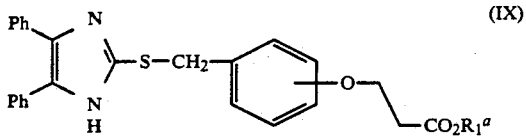

wherein R$_1{}^a$ is lower alkyl; or (b) esterifying a compound of Formula X

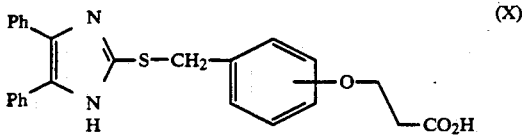

or;

(c) alkylating 4,5-diphenyl-2-imidazolethiol with a compound of Formula XI

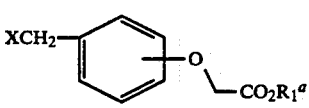

wherein R$_1{}^a$ is lower alkyl and X is halogen or an aryl sulfonate.

The compounds of Formula VIII have pharmacological properties similar to those of Formula I and II compounds. In vitro inhibition of human platelet aggregation test results for the compounds of Examples 4 and 5 are given hereinafter.

TABLE 2

Inhibition of Human Platelet Aggregation of Formula VIII Compounds (IC$_{50}$ mcg/ml)

TABLE 2-continued

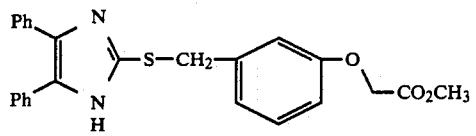

| Example | R$_1$ | Vs ADP mcg/ml |
|---|---|---|
| 4 | CH$_3$ | 0.42 |
| 5 | H | 0.41 |

EXAMPLE 4

Methyl [3-[[(4,5-diphenyl-1H-imidazol-2-yl)thio]methyl]-phenoxy]acetate

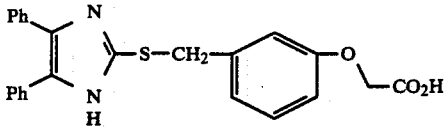

Sodium hydride (684 mg of a 50% dispersion, 14 mmol) was washed three times with hexane and covered with DMF (60 mL). 4,5-Diphenyl-1-imidazolethiol (3 g, 12 mmol) was added to afford a yellow solution after hydrogen evolution had ceased. Methyl (3-chloromethylphenoxy)acetate (2.68 g, 12.5 mmol) was added and the mixture stirred at room temperature for 1.5 hours and then at 100° C. for 0.5 hour. After cooling, the mixture was diluted with water and extracted with diethyl ether (3 times). The combined extracts were washed with water (3 times), dried and concentrated in vacuo. Crystallization of the residual solid from a mixture of hexanes and CH$_2$Cl$_2$ afforded methyl [3-[[(4,5-diphenyl-1H-imidazol-2-yl)thio]methyl]phenoxy]-acetate (3.00 g, 58%), m.p. indistinct.

Anal. Calcd. for $C_{25}H_{22}N_2O_3S$: C, 69.75; H, 5.15; N, 6.51. Found: C, 69.79; H, 5.23; N, 6.24.

$^1$H-NMR (CDCl$_3$) delta: 3.72 (3H, s), 4.13 (2H, s), 4.56 (2H, s), 6.75 to 6.80 (3H, m) and 7.10 to 7.50 (12H, m).

EXAMPLE 5

[3-[[(4,5-Diphenyl-1H-imidazol-2-yl)thio]methyl]-phenoxy]acetic Acid

A mixture of methyl [3-[[(4,5-diphenyl-1H-imidazol-2-yl)thio]methyl]phenoxy]acetate (2.00 g, 4.6 mmol), lithium hydroxide monohydrate (586 mg, 14 mmol), methanol (35 mL) and water (10 mL) was stirred at room temperature for 2 hours. The solvent was evaporated, the residue diluted with water and 2N HCl solution added to pH=7. A white solid was filtered off and recrystallized from aqueous DMF to give [3-[[(4,5-diphenyl-1H-imidazol-2-yl)thio]methyl]phenoxy]acetic acid (1.33 g, 69%), m.p. 233°–235° C.

Anal. Calcd. for $C_{24}H_{20}N_2IO_3S$: C, 69.21; H, 4.84; N, 6.73. Found: C, 69.43: H, 4.92; N, 6.92.

$^1$H-NMR (DMSO-D$^6$) delta: 4.34 (2H, s), 4.60 (2H, s), 6.77 (1H, dd, J=8 Hz, J'=2 Hz), 6.90 to 7.00 (2H, m), 7.05 to 7.60 (12H) and 12.40 to 13.00 (1H, bs).

What is claimed is:

1. A compound of Formula I $$HET_1-(CH_2)_nCO_2R \quad (I)$$

wherein n is 6 to 9:

R is hydrogen or lower alkyl or an alkali metal ion;

and

HET$_1$ is the heterocyclic radical

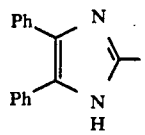

4,5-diphenyl-1H-imidazol-3-yl.

2. A compound of Formula II

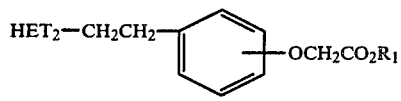

wherein

R$_1$ is hydrogen, lower alkyl or an alkali metal ion, and the radical —OCH$_2$CO$_2$R$_1$ is attached in the 3 or 4 ring position;

HET$_2$ is the heterocyclic radical

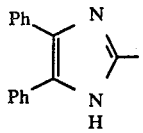

4,5-diphenyl-1H-imidazol-2-yl.

3. The compound of claim 2 which is methyl [3-[2-(4,5-diphenyl-1-imidazol-2-y)ethyl]phenoxy]acetate.

4. The compound of claim 2 which is [3-[2-(4,5-diphenyl-1H-imidazol-2-yl)ethyl]phenoxyacetic acid.

5. The method for inhibiting blood platelet aggregation in a mammal which comprises administering a therapeutically effective amount of a compound of claim 1.

6. The pharmaceutical composition for inhibiting blood platelet aggregation comprising a therapeutically effective amount of a compound of claim 1 and a pharmaceutical carrier.

7. The method for inhibiting blood platelet aggregation in a mammal which comprises administering a therapeutically effective amount of a compound of claim 2.

8. The pharmaceutical composition for inhibiting blood platelet aggregation comprising a therapeutically effective amount of a compound of claim 2 and a pharmaceutical carrier.

9. A compound of Formula VIII

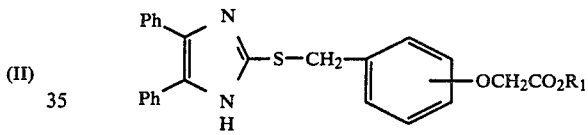

wherein R$_1$ is hydrogen, lower alkyl or an alkali metal ion, and the radical —OCH$_2$CO$_2$R$_1$ is attached in the 3 or 4 ring position.

10. The compound of claim 9 which is methyl [3-[[(4,5-diphenyl-1H-imidazol-2-yl)thio]methyl]-phenoxy]-acetate.

11. The compound of claim 9 which is [3-[[(4,5-diphenyl-1H-imidazol-2-yl)thio]methyl]phenoxy]acetic acid.

* * * * *